United States Patent
Kahl et al.

(10) Patent No.: US 7,204,922 B1
(45) Date of Patent: Apr. 17, 2007

(54) METHOD AND DEVICE FOR THE ELECTROPHORETIC SEPARATION OF PARTICLES, ESPECIALLY OF MACROMOLECULES, BY ELECTROPHORESIS

(76) Inventors: Johan-Valentin Kahl, Amallenstrasse 49a, München (DE) 80799; Julia Nissen, Pelssenbergstr, 4, München (DE) 81547; Joachim Rädler, Römerholweg 51, Garching (DE) 85748; Roman Zantl, Odeonsplatz 2, München (DE) 80539; Berenike Maier, Rathausstrasse 34, Karisfeld (DE) 85757; Ulf Rädler, Marchgrabenplatz 1a, München (DE) 80805; Andres Hohner, Leberbiümchenstr, 18, München (DE) 80995; Reinhard Galneder, Guerickestr, 19, München (DE) 80805

( * ) Notice: Subject to any disclaimer, the term of this patent is extended or adjusted under 35 U.S.C. 154(b) by 0 days.

(21) Appl. No.: 10/049,245

(22) PCT Filed: Jul. 26, 1999

(86) PCT No.: PCT/EP00/07206

§ 371 (c)(1),
(2), (4) Date: Jun. 24, 2002

(87) PCT Pub. No.: WO01/07150

PCT Pub. Date: Feb. 1, 2001

(30) Foreign Application Priority Data

Jul. 26, 1999 (DE) ................. 199 35 028

(51) Int. Cl.
*G01N 27/26* (2006.01)

(52) U.S. Cl. ..................... 204/450; 204/600

(58) Field of Classification Search ............... 204/450, 204/600; 436/514–516; 422/82.02
See application file for complete search history.

(56) References Cited

U.S. PATENT DOCUMENTS

| | | | |
|---|---|---|---|
| 5,039,386 A | | 8/1991 | Margolis |
| 5,059,294 A | | 10/1991 | Lizardi |
| 5,066,382 A | | 11/1991 | Weinberger et al. |
| 5,264,098 A | | 11/1993 | Chevigne |
| 5,423,966 A | | 6/1995 | Wiktorowicz |
| 5,427,663 A | | 6/1995 | Austin et al. |
| 5,552,155 A | * | 9/1996 | Bailey et al. ............... 424/450 |
| 5,630,924 A | | 5/1997 | Fuchs et al. |
| 5,637,201 A | * | 6/1997 | Raguse et al. ......... 204/403.06 |
| 5,736,342 A | * | 4/1998 | Van Wie et al. ............. 435/7.2 |
| 5,846,394 A | | 12/1998 | Burlatsky et al. |
| 6,007,978 A | * | 12/1999 | Goodrich et al. ............... 435/2 |
| 6,013,165 A | * | 1/2000 | Wiktorowicz et al. ...... 204/456 |
| 6,228,326 B1 | * | 5/2001 | Boxer et al. ............. 422/82.02 |
| 6,284,163 B1 | * | 9/2001 | Stowell et al. ............... 264/4.1 |

FOREIGN PATENT DOCUMENTS

| | | |
|---|---|---|
| DE | 4323487 A1 | 1/1995 |
| EP | 0396053 A2 | 11/1990 |
| EP | 0398388 A1 | 11/1990 |
| EP | 0459707 A1 | 12/1991 |
| EP | 0976758 A1 | 2/2000 |
| WO | WO 91/14489 A1 | 10/1991 |
| WO | WO 96/23213 A1 | 8/1996 |
| WO | WO 96/42012 A1 | 12/1996 |
| WO | WO 98/58248 * 12/1998 | ............. 205/777.5 |

OTHER PUBLICATIONS

J. T. Groves et al., "Electrical Manipulation of Glycan-Phosphatidyl Inositol-Tethered Proteins in Planar Supported Bilayers." Biophys. J. 71, 2716-2723 (1996).*

T. Hianik et al, "Stabilization of bilayer lipid membranes on solid supports by trehalose" Bioelectrochem. Bioenerg., 39, 299-302. (1996).*

Von Oudenaarden et al.; Brownian Ratchets: Molecular Separations Inlipid Bilayers Supported on Patterned Arrays; Aug. 13, 1999; Science; vol. 285; pp. 1046-1048.

* cited by examiner

Primary Examiner—Nam Nguyen
Assistant Examiner—Jeffrey Barton
(74) Attorney, Agent, or Firm—IP Strategies

(57) ABSTRACT

The present invention provides a method for the electrophoretic separation of particles, especially of macromolecules, comprising the steps of applying the particles to be separated on a substrate supported membrane, such that the particles are mobile across the surface of the substrate supported membrane; providing an electrical field such that electrical fields are formed along the surface across which the particles are mobile; and temporarily modifying the electrical field and/or adding a substrate supported membrane having a structured surface, wherein the direction and/or the strength of the electrical field are temporarily modified and/or wherein the substrate supported membrane is structured so that a force is acting on the particles that leads to a movement depending on the length of the particles. Moreover, a substrate is provided, in particular, for supporting a membrane during the performing of the inventive methods, that comprises an optically transparent material. Moreover, the invention provides a substrate supported membrane for carrying out the inventive methods including an inventive substrate as defined in the claims and a fluid lipid membrane. Moreover, the present invention provides a microchannel electrophoresis chamber having at least one channel with a bottom surface including an inventive substrate, and an electrode assembly.

20 Claims, 3 Drawing Sheets

METHOD AND DEVICE FOR THE ELECTROPHORETIC SEPARATION OF PARTICLES, ESPECIALLY OF MACROMOLECULES, BY ELECTROPHORESIS

CROSS-REFERENCE TO RELATED APPLICATIONS

This is the National Stage entry of International Application No. PCT/EP00/07206, filed Jul. 26, 2000, which claims benefit of foreign priority from German Application No. DE 199 35 028.0.

FIELD OF THE INVENTION

The present invention relates to a method and an apparatus for separating particles, in particular, macromolecules, such as DNA, RNA macromolecules, DNA, RNA oligomers and proteins by electrophoresis.

DESCRIPTION OF THE PRIOR ART

Methods using electrophoresis are preferably employed in molecular biology, genetic engineering and in the medical field to separate macromolecules having a different charge and a different size.

In the art substantially two different methods of the electrophoresis for the separation of macromolecules are known, namely the so-called gel electrophoresis and the capillary gel electrophoresis. In gel electrophoresis a gel applied to a plate is used; in capillary gel electrophoresis a gel-like polymeric solution in a capillary is provided.

In both the gel and capillary gel electrophoresis one takes advantage of the fact that macromolecules having a different charge and size migrate with a different velocity in a gel when influenced by an external electrical field, and bands are thereby generated each containing a species of the different macromolecules, i.e., the macromolecules having the same charge or the same size. The location of the bands is optically readout by color techniques or UV light absorption.

In order to readout the bands a layer of a coloring agent is applied to the gel and is maintained there at a precisely controlled temperature for a determined time. Thereafter the coloring reaction is prevented by withdrawing the water from the gel.

Typically, agarose, cellulose acetate or acrylamide are used as gels. Gel electrophoresis and capillary gel electrophoresis are used, for example, in DNA analysis in the medical research and diagnosis. By means of restriction fragment analysis a prediction can be made about, for example, the genetic information, and for this reason gel electrophoresis has gained great importance for the diagnosis of genetically determined diseases.

Substantial disadvantages of methods using gel electrophoresis and capillary gel electrophoresis reside in the fact that, on the one hand, a significant amount of time is required for preparing and carrying out electrophoresis, and, on the other hand, that a large amount of sample material is required for the analysis.

In particular, in both methods the usual electrophoresis paths are relatively long. This entails migration times of approximately two hours. Furthermore, prior to the actual electrophoresis process, the gel has to be prepared, for example, it has to be heated. Automation of the this process is, in principle, possible is, however, accompanied by great effort, since the required equipment leads to high costs. Therefore, electrophoresis is often carried out manually, thereby additionally contributing to an increased time consumption.

Moreover, the conventional method may not arbitrarily be scaled down to, for example, reduce the amount of samples required.

In view of the above mentioned disadvantages, the present invention is directed to a method and apparatuses for carrying out a method in which, on the one hand, time consumption for the separation of macromolecules by means of electrophoresis may be reduced and which, on the other hand, are appropriate for scaling down so that already small amounts of samples are sufficient for the analysis.

SUMMARY OF THE INVENTION

The above-mentioned object is solved by a method for the electrophoretic separation of particles, in particular, of macromolecules, comprising applying the particles to be separated on a substrate-supported membrane such that the particles are mobile across the surface of the substrate-supported membrane. The method further comprises providing an electrical field such that directions of the electrical field are oriented along the surface across which the particles are mobile. Additionally, the method includes temporarily modifying the electrical field and/or using a substrate-supported membrane having a structured surface, wherein the electrical field is temporarily modified and/or the substrate-supported membrane is structured in such a manner that a force is acting on the particles which leads to a movement depending on the length of the particles.

By means of a defined selection of the applied electrical field and/or a corresponding structuring of the membrane, a force acts on the particles that depends on the length of the macromolecules, and consequently a different path length in the electrical field is obtained for macromolecules depending on their size. Contrary to the prior art, in the present method, the running times may be significantly reduced in that the macromolecules no longer have to propagate in the gel, but instead are bound at the surface of the membrane, yet are otherwise freely movable. The high degree of mobility of the macromolecules on the membrane, therefore, leads to a significant reduction of the time period necessary to carry out electrophoresis. Furthermore, time consumption for the preparation of a membrane is remarkably reduced compared to the time consumption required for casting a gel.

In a further preferred embodiment of the present invention, a fluid lipid membrane is used as the substrate-supported membrane. By using such a membrane, it is insured that, one the one hand, the particles are bound to the membrane and, on the other hand, the particles have a sufficient degree of mobility on the surface of the membrane. The three-dimensional movement known from the prior art may accordingly be reduced to a quasi-two-dimensional movement. Such membranes may comprise, for example, PEG functionalized lipids or DAC-Chol: 3-beta-(N—(N,N'-Dimethylaminoethan)-carbamoyl) (-cholesterolhydrochlorid). Preferably, a cationic fluid lipid membrane may be used for this purpose. By means of such a membrane typically negatively charged DNA, RNA macromolecules and DNA, RNA oliogomeres, respectively, may be bound to the membrane.

According to a further embodiment amphiphilic macromolecules may be used for building up the membrane. Amphiphilic macromolecules are characterized in that they form monolayers and bilayers in an aqueous solution.

According to a further embodiment of the previous method, a fluid lipid membrane may be used that comprises monolayers or bilayers including charged lipids. Accordingly, on the one hand, good adherence of the membrane to the substrate is guaranteed and, on the other hand, binding of the macromolecules to the membrane is insured. Moreover, in this way, the membrane may be formed relatively thin so that the observation of the bands with optical means is possible without any problems.

According to a first alternative of the above described method, a pulsed electrical field is used. The macromolecules of different size that have been applied to the membrane initially perform an unordered Brownian movement. If then a pulsed electrical field is applied, the various macromolecules are oriented along the lines of the electrical flux during the first pulse. This orientation occurs depending on the size of the macromolecules, wherein the smaller macromolecules are aligned more rapidly than are the larger ones. The macromolecule starts its movement in the direction of a field gradient once the macromolecule is oriented correspondingly to the electrical field. As a consequence, smaller macromolecules start moving in the electrical field earlier than larger macromolecules. During the time period between the first and the second pulse, again an unordered Brownian movement of the macromolecules occurs; however, due to the greater migration distance the smaller macromolecules have moved during the first pulse, they perform their unordered movement at a different location than do the larger macromolecules. If now the second pulse is applied, again, orientation of the macromolecules along the field line takes place. Again, smaller macromolecules are aligned more rapidly than larger macromolecules and again move a larger distance in the electrical field during the second pulse. As a result, in this way a separation of the macromolecules can be achieved depending on their size.

According to a second alternative of the above described method, an alternating field can be used on which a time constant field is superposed. The macromolecules substantially moved along the lines of electrical fluxes driven by the time constant field. However, the movement in this field is also influenced by the alternating field in which the macromolecules are oriented. Since, analogous to the above case, the macromolecules are oriented in the alternating field with a rate depending on their size and also move in the alternating field, a smaller macromolecule again moves a larger distance per time unit. In that the macromolecules are not only oriented under the influence of the alternating field, but also move in the alternating field, in total, the macromolecules perform a zigzagging movement on the surface of the membrane.

Advantageously, in this case, the alternating field and the time constant field may be superimposed in a crosswise fashion. In this case, a symmetrical path of the macromolecules on the membrane is obtained.

In the methods according to the first and second alternatives, additionally a substrate including ribs on its surface may be used for supporting the membrane. By this measure, the movement and especially the orientation of the macromolecules in the electrical field in dependence on their size is influenced even more intensely. In particular, the frictional force during the orientation increases more intensely for larger macromolecules than for smaller ones, which, in total, leads to a further discrimination in view of the size of the macromolecules.

For carrying out the method, a substrate has proven to be appropriate the ribs of which exhibit a periodicity in the range from 2 nm to 200 nm. Advantageously, the height of the ribs thereby ranges from 0.1 nm to 10 nm.

According to a third alternative of the above described method, a time constant field may be used, having a direction substantially perpendicular to the ribs, when a membrane is used that is provided on a substrate having ribs. Accordingly, larger macromolecules experience a larger frictional force than the smaller macromolecules, resulting in a smaller velocity of these larger macromolecules in the direction of the field. Consequently, a separation of the macromolecules depending on their length is also achieved.

According to a further preferred embodiment of all of the above described methods, a membrane is used having an exclusion area in which a movement of the particles is not possible or on the boundary of which the macromolecules are stopped. By the application of a corresponding electrical field prior to performing the actual electrophoresis the particles may accordingly be collected in a narrow region in front of this exclusion area. Thereby, a clearly defined start point and a narrow range of the movement taking place during the electrophoresis are defined. This results in an improved resolution of the method.

When using a fluidal membrane, the exclusion area may be realized by a non fluid area in the fluid membrane. This non-fluid area may be obtained, for example, in that the substrate is coated with a material on which the actual fluid membrane is not fluid. For example, $Al_2O_3$ is appropriate for this purpose. Such an exclusion area can also be obtained in that a different material is applied to the substrate so that in this area no fluid membrane can form. For instance, $Al_2O_3$ is suitable for this purpose.

The above described methods can be employed in a method for observing an electrophoretic separation. For this purpose, preferably, digitized image data are recorded by, for example, a video camera coupled to an optical microscope while performing the electrophoretic separation. Thereafter, these recorded image data may be evaluated by using a computer.

Compared to the prior art, this embodiment offers the large advantage that also dynamic processes may be observed in a simple manner. Accordingly, it is possible, for example, to observe DNA-cutting enzymes during their activity.

The above described methods for the electrophoretic separation are, as previously explained, especially suited for separation of DNA, RNA macromolecules, DNA, RNA oligomers. Additionally, with this method a plurality of other macromolecules, such as proteins, may also be investigated.

Advantageously the so-called iso-electrical focusing may be used to improve the resolution. Hereby, the particles migrate in a pH gradient up to a pH value corresponding to their iso-electrical point at which they exhibit a zero net charge. That is, the migration speed at this point is also zero. In the one-dimensional protein electrophoresis the pH gradient field is parallel to the electrical field. In the two-dimensional electrophoresis the pH gradient is perpendicular to the applied field.

According to the present invention, a substrate is provided in particular for supporting the membrane during the performing of one of the above described methods, which is comprised of an optical transparent material. With such a substrate it is possible, especially in combination with the relatively thin membrane, to directly observe or to record, using a video camera, the bands of the different sizes of the macromolecules, which have formed after the electrophoretic separation. This provides the advantage that the macromolecules may be maintained in their native state during analysis, thereby allowing the macromolecules to be available for analysis steps to be performed later on, such as a DNA hybridization.

According to a further embodiment the substrate may comprise glass as an optically transparent material.

Alternatively, plastics may also be used as an optically transparent material. In particular, plastics such as PC, PMMA, PS, PE or plastics of cyclic olefins may also be used for this purpose. Since plastics may be processed more simply than glass, plastics are especially suited when the substrate shall include complex structures, for example for the performing of the method with a structured substrate.

In the method in which a structured substrate is employed especially a substrate is appropriate that includes a surface having ribs formed therein. Preferably, the ribs and the substrate exhibit a periodicity ranging from 2 nm to 200 nm. As a height of the ribs, a height ranging from 0.1 nm to 10 nm has proven to be suitable.

The essential point of structured substrate resides in the fact that macromolecules provided on a membrane that is applied on such a substrate experience a frictional force that depends on the size of the macromolecules. Therefore, differently formed structures leading to this effect may be used.

Although these substrates may advantageously be used in the above described methods, these substrates may also be employed in other applications, such as in expanding or orienting of macromolecules. This is especially true for the substrates having a structured surface such as the rib-shaped surface.

Moreover, according to the present invention a substrate supported membrane is provided that is especially suited for performing the above described methods and which comprises one of the previously described substrates and a fluid lipid membrane applied on the corresponding substrate.

By means of this substrate supported membrane simple means are provided for the carrying out of the above described methods.

Advantageously, the substrate supported membrane may comprise a fluid lipid membrane having cationic lipids. Advantageously amphiphilic macromolecules may also be used for forming the membrane. Furthermore, the fluid lipid membrane may comprise bilayers of charged lipids. Moreover, the fluid membrane of the substrate supported membrane may comprise at least one non-fluid area.

With these advantageous embodiments the advantages may be attained that have been discussed with respect to the methods. To avoid any repetitions it is referred to the corresponding parts of the description of the present methods.

According to a further embodiment the fluid lipid membrane of the substrate supported membrane may be dried up. Therefore, the substrate having the membrane dried up may be stored. For usage the substrate supported membrane has only to be swelled in water and/or a buffer solution. With membranes prepared in such a manner possible errors and deviations in producing the membrane, in particular in preparing the solutions for the membrane, may be avoided, so that the reproducibility of results is increased.

Moreover, in accordance with the present invention, there is additionally provided a microchannel electrophoresis chamber comprising at least one channel the bottom surface of which includes one of the previously described substrates wherein the microchannel chamber comprises an electrode assembly.

In such a microchannel electrophoresis chamber the various process steps such as determination of the start point, the electrophoretic separation of particles by the movement in an electrical field and the optical evaluation of the bands may be integrated. Consequently, the present method is significantly simplified compared to the prior art technique that required to carry out these process steps in different stages and in different work places. Moreover, in such a microchannel electrophoresis chamber it is possible to expand, to manipulate and to simultaneously make macromolecules available for optical methods.

Preferably, hereby each channel has a width in the range from 1 micrometer to 10 millimeters and depth in the range from 1 μm to 5000 μm.

According to a preferred embodiment the microchannel electrophoresis chamber may comprise a plurality of channels arranged in the form of a two-dimensional matrix. It is thus possible to carry out a plurality of experiments at the same time.

According to a preferred embodiment of the microchannel electrophoresis chamber the electrode assembly may comprise two electrodes that are provided at the respective longitudinal ends of each channel. This embodiment leads to a further simplification of the experimental set up. Hereby, the electrodes may already be integrated in the microchannel electrophoresis chamber and the microchannel electrophoresis channel has merely to be connected at the measurement location. Moreover, since the electrodes are already provided in the microchannel electrophoretic chamber, a predetermined arrangement with respect to each channel and therefore also with respect to the membrane may be realized, thereby resulting in a fixedly defined field with respect to the membrane. Thereby, a further scaling-down may be obtained compared to the prior art, since in the prior art the scaling-down is limited due to the position accuracy of the electrical field with respect to the membrane.

According to a further embodiment the electrode assembly may alternatively or additionally comprise two electrodes extending longitudinally along the channel direction at both sides of each channel. This embodiment is especially appropriate for the above described method in which an alternating field and a time constant field provided in a crossed manner thereto is used. It is to be understood that also in this case the advantages may be obtained that have been discussed with reference to the above described electrode assembly.

In the above described microchannel electrophoresis chamber the substrate may be coated with a fluid lipid membrane. This fluid lipid membrane may comprise cationic lipids. Advantageously, the fluid lipid membrane may comprise amphiphilic macromolecules. Moreover, the fluid lipid membrane may include bilayers of charged lipids, the fluid lipid membrane may be provided in a dried form and/or may at least comprise a non-fluid area.

By these special embodiments the advantages already discussed with reference to the various methods and the various substrate supported membranes may also be attained. In order to avoid any redundancies it is merely referred to the corresponding explanations of these features with respect to the methods and the substrate supported membranes.

BRIEF DESCRIPTION OF THE DRAWINGS

In the following the present invention will be describes with reference to various embodiments by referring to the accompanying drawings in which:

FIG. 1 depicts an embodiment of a microchannel electrophoresis chamber for explaining a first embodiment of the method for the electrophoretic separation of particles according to the present invention. A microchannel electrophoresis chamber 1 comprises a chamber body 2, in which a channel 3 is provided. The bottom surface of channel 3 is hereby provided in form of a non-structured substrate 4. The substrate 4 is optically transparent comprising, for example, glass, plastics such as PMMA, PC, PS, PE or similar materials. Moreover, the substrate is thinned down to approximately 100 µm.

Because of this, the microchannel electrophoresis chamber 1 is directly available for optical read out methods.

The substrate 4 may be inserted in a corresponding opening in the chamber body 2 or as in the present case, may directly be formed as a part of the chamber body 2. To this end, a channel having a corresponding depth in a range of 1 µm to 5000 µm may be provided in the chamber body.

Figure 1:
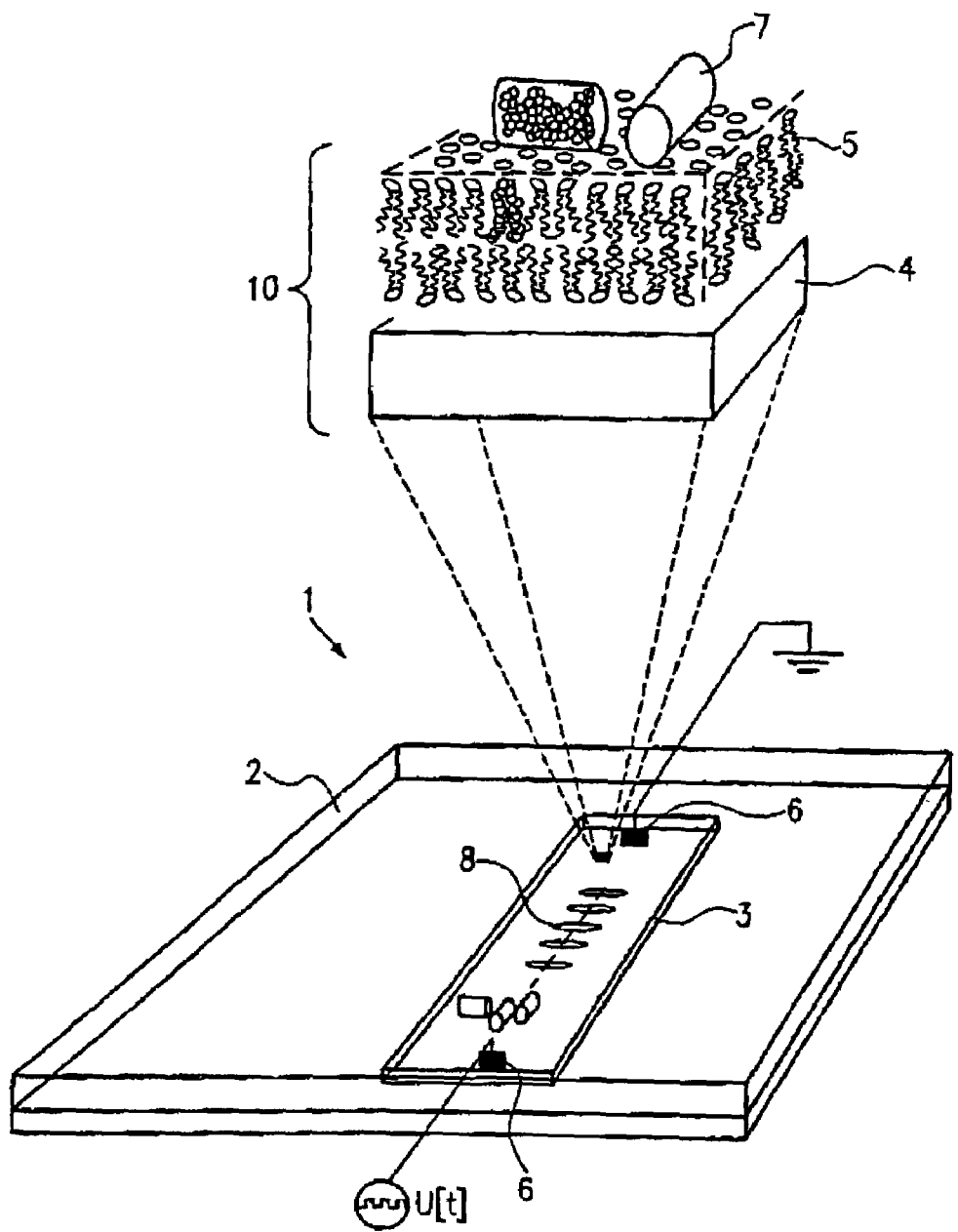
FIG. 1: depicts an embodiment of a microchannel electrophoresis chamber for explaining a first embodiment of the method for the electrophoretic separation of particles in accordance with the present invention.

A fluid membrane 5 is applied on the substrate as is especially depicted in the enlarged view of FIG. 1. In the present embodiment, the membrane 5 is provided in form of a bilayer lipid membrane, such as a DPOC/DOTAP membrane.

Moreover, the electrophoresis chamber comprises an electrode assembly 6 including two electrodes provided at the longitudinal ends of the channel 3, wherein the electrodes comprise conventional materials such as platinum, gold, Ag/AgCl and the like. One of these electrodes is grounded, whereas a pulsed voltage in a range of 2 to 1000V is applied to the other electrode, as will be explained in the following.

As is further depicted in the enlarged view, two macromolecules are provided on the membrane 5.

The entire arrangement depicted in FIG. 1, i.e. the membrane 5, the macromolecules 7 and the substrate 4 are within a liquid, for example water or a molecule-stabilizing buffer.

In the following a first embodiment of the method for the electrophoretic separation of macromolecules is described with reference to FIG. 1.

In the embodiment depicted in FIG. 1 and as also indicated in FIG. 1, and electrical field is used. The macromolecules 7 of different size that have been applied on the membrane 5 perform an unordered Brownian movement between the voltage pulses, that is, at a voltage of 0V. During the voltage pulses, however, the various macromolecules are initially aligned along the lines of electrical fluxes. This alignment or orientation occurs depending on the size of the macromolecules, wherein the smaller macromolecules are oriented more rapidly than the larger ones. After a macromolecule is oriented or aligned in the electrical field, it also starts moving in the electrical field during the voltage pulses and it moves in the direction of the electrical field. Since smaller macromolecules are oriented in the electrical field more rapidly than larger macromolecules, the smaller macromolecules start moving in the electrical field earlier and therefore move the larger distance in the field during the voltage pulses than the larger macromolecules.

During the application of a pulsed voltage the macromolecules therefore move, depending on their charge and size respectively, over different distances on the membrane 5 in the channel 3 and they collect in so-called bands 8 according to their charge or size as is depicted in FIG. 1.

Figure 2:
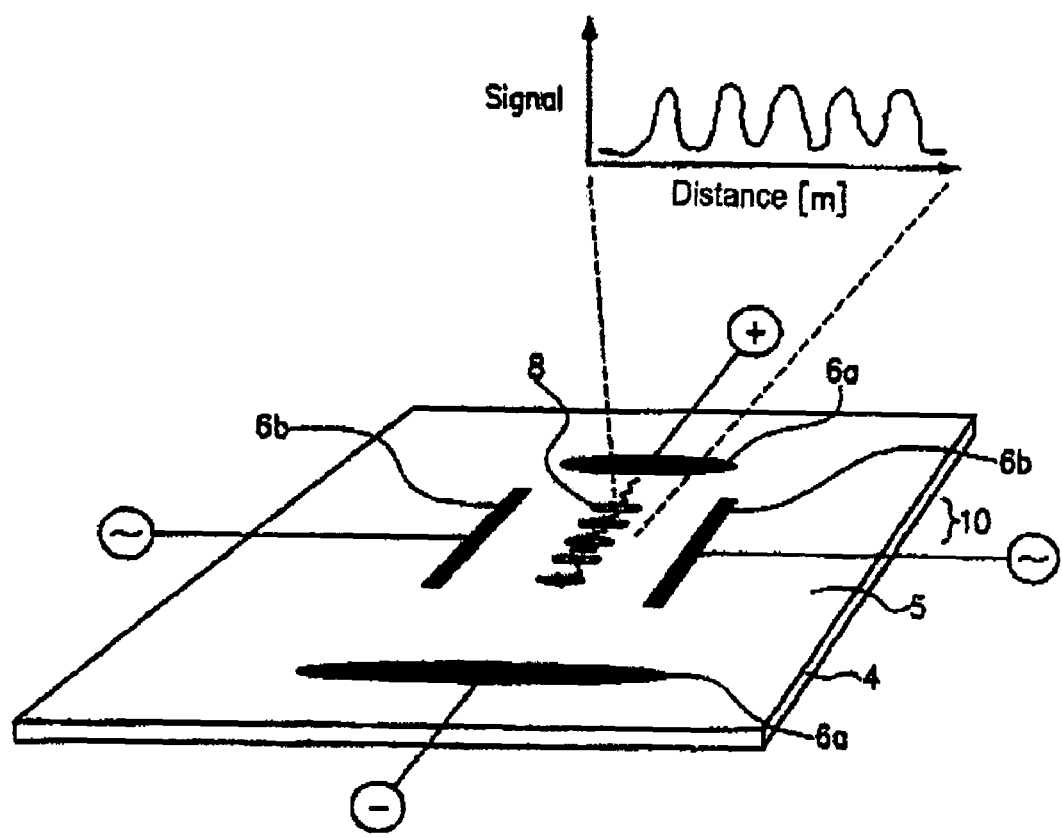
FIG. 2: shows a first embodiment of a substrate supported membrane for explaining a second embodiment of the method for the electrophoretic separation of particles according to the present invention.

FIG. 2 shows a first embodiment of a substrate supported membrane 10 for explaining a second embodiment of the method for the electrophoretic separation of particles according to the present invention. In the following, merely the differences between both arrangements are described so as to avoid any repetition. Hereby, the same numerals indicate the same components of the corresponding arrangement.

The substrate supported membrane 10 in FIG. 2 differs from the arrangement depicted in FIG. 1 substantially by the electrode assembly. Moreover, the substrate supported membrane 10 is provided in a chamber body of the channel floor. The remaining components correspond to those of the structure depicted in FIG. 1; for the description thereof, it is therefore referred to the corresponding discussion provided above.

The electrode assembly of the substrate supported membrane depicted in FIG. 2 comprises two electrodes 6a and two electrodes 6b. A constant voltage (DC) which preferably ranges from 2 to 1000V is applied to the electrodes 6a and an alternating voltage (AC) preferably in the range of 2 to 1000V and having a frequency in the range of 0.1 to 200 Hz is applied to the electrodes 6b.

As in the arrangement shown in FIG. 1, also in this case the membrane, the substrate and the macromolecules are provided in a liquid, for example in water.

In the following, a second embodiment of the method for the electrophoretic separation of macromolecules by using a substrate supported membrane as shown in FIG. 2 will be described.

By means of the time constant field caused by the electrodes 6a, the macromolecules move essentially in the direction of the field gradient. The motion in this field is however also influenced by the alternating field created by the electrodes 6b, in which the macromolecules are oriented and also move. Since the macromolecules, analogous to the above case, are oriented and move in the alternating field depending on the size of the macromolecules, the smaller macromolecules again move a larger distance per time unit. Since the macromolecules not only are oriented under the influence of the alternating field, but also move in the alternating field, they perform a zig-zag movement on the surface of the membrane as is indicated in FIG. 2.

As in the first method, the macromolecules also gather in the bands 8, which are indicated on the membrane on FIG. 2 and which are additionally presented in a histogram (the histogram depicts the number of molecules versus the distance moved on the substrate supported membrane), since the macromolecules move different distances according to the size and charge, respectively.

Figure 3:
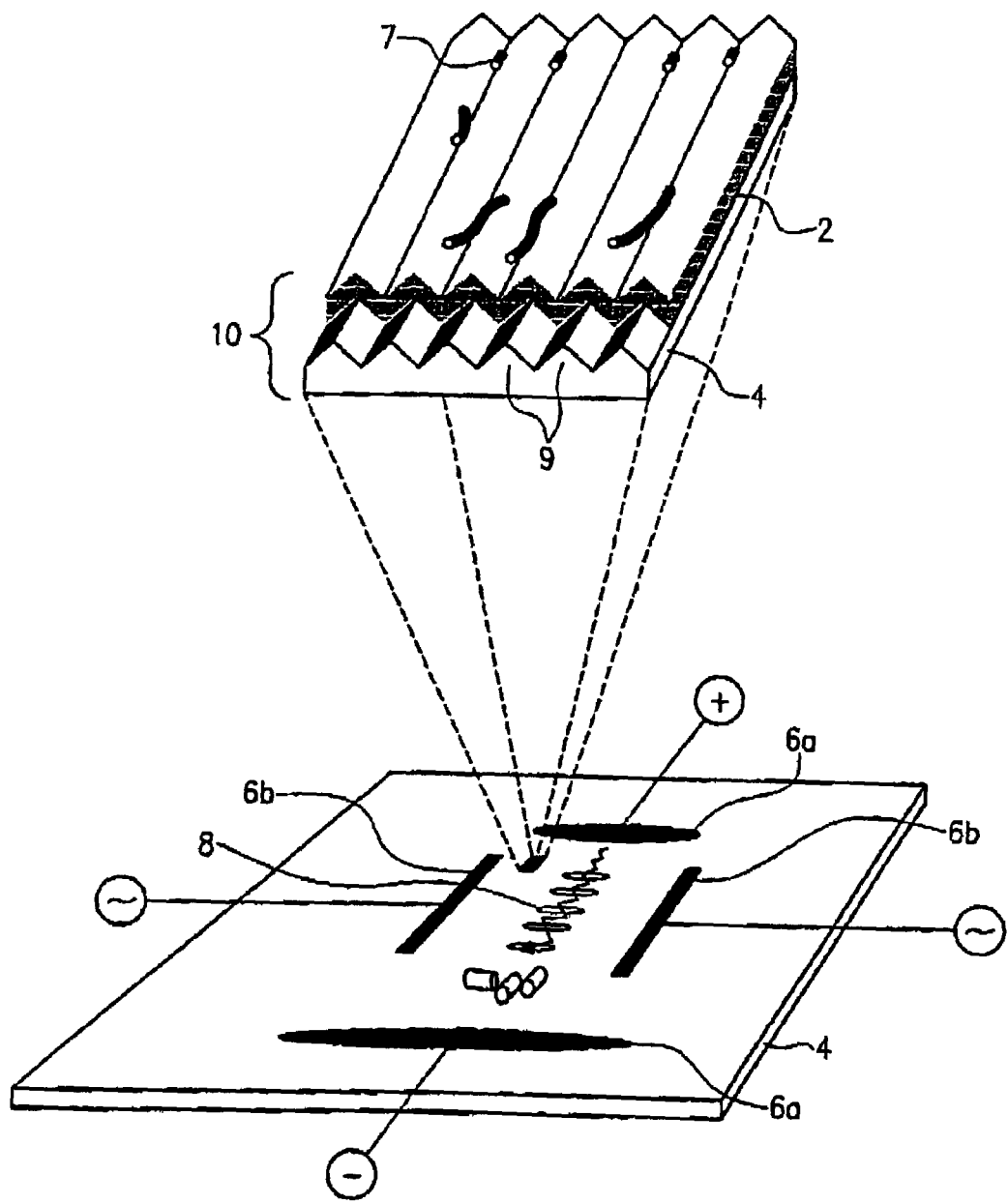
FIG. 3: depicts a second embodiment of a substrate supported membrane for explaining a third embodiment of the method for the electrophoretic separation of particles according to the present invention.

FIG. 3 depicts a second embodiment of a substrate supported membrane for explaining a third embodiment of the method for the electrophoretic separation of particles according to the present invention.

This embodiment differs from the substrate supported membrane shown in FIG. 2 in that the surface of the substrate 4 is provided with ribs 9. The remaining arrangement of the embodiment corresponds to that depicted in FIG. 2, and therefore it is referred to the explanation of the latter embodiment to avoid any repetition.

In the embodiments of FIG. 3 a substrate is used the ribs of which exhibit a periodicity in the range of 2 nm to 200 nm. The height of the ribs thereby ranges from 0.1 nm to 10 nm. In a substrate comprising the above indicated plastics, the structuring can be formed by, for example, imprinting a die containing the negative of the desired form. To this end, the plastic is preferably heated. A silicon wafer cut in the (111) plane and etched with KOH may be used as the die.

By employing the substrate 4 having the ribs 9, the movement and, in particular, the orientation in the electrical field of the macromolecules, depending on the size of the macromolecules, on a membrane applied on a such a substrate is influenced even more intensely. Especially, the frictional force for larger macromolecules during their orientation is increased more intensely than that for smaller macromolecules leading, in total, to a further discrimination with respect to the size of the macromolecules.

For a further explanation of the present invention, various examples will be described which have been performed with the above described means.

EXAMPLE 1

Preparation of a Substrate Supported Membrane by Vesicular Fusion

In example 1 the substrate supported membrane was realized by manufacturing of a cationic bilayer of lipids by vesicular fusion of a glass support. To this end, for example, lipids solved in chloroform were mixed. A typical ratio of DOPC/DOTAP is 9/1. This solution was dried up and then the lipids were swelled with water or a buffer solution, such as HEPES 10 mM, NaCL 10 mM, EDTA 1 mM. The lipid concentration was approximately 1 mg/ml. This solution was exposed to sonic waves with a blow pipe sonic wave means for 1 to 2 minutes. The surface to be coated was heated prior to the actual vesicular fusion process to be greatly hydrophilic. Suitable for these purposes is a treatment of 1 minute with a 5M KaOH solution. For the filling of a chamber, as previously described, a vesicular solution of approximately 2 ml was provided to the chamber. After approximately 2 hours, the chamber was thoroughly purged with a buffer solution to remove the excess lipid. After this treatmeant, a bilayer having a thickness of approximately 4 nm remained in the chamber. Between the bilayer and the substrate, an approximately 0.1 nm thick water layer was formed. In this example, the membrane had a lateral self diffusion constant of approximately 1 $\mu m^2/s$.

Since, in the present example, the electrophoretic separation should be evaluated by microscopy with high resolution, a transparent optically inert substrate or a chamber floor was used, the thickness of which was between 100 and 200 $\mu m$.

Separation of the DNA by Means of Pulsed Fields

The macromolecules to be separated, for example, DNA 80 bp (base pairs) and 40 bp were also inserted into the chamber.

Double strand DNA of the length of 80 bp exhibited a self diffusion constant of 0.2 $\mu m^2/s$ on the fluid membrane of the present example, whereas DNA having a length of 40 bp exhibited a diffusion constant of 0.4 $\mu m^2/s$.

By the application of a pulsed field between 0.1 V/cm and 100V/cm, the DNA macromolecules separate. Advantage was taken from the fact that the DNA oligomers were randomly oriented by self-rotation diffusion after each turn off of the field. This effect breaks up the proportional ratio between the number of DNA base pairs and the mobility.

To avoid any polarization of the electrodes, platinum electrodes or Ag/AgCl electrodes that had been blackened were used. Depending on the chamber size, salt contents of the buffer solution and the applied voltage, a current between 0.1 $\mu A$ and 10 $\mu A$ is flowing. The electrical field was applied for approximately 10 minutes.

Display of the DNA Bands by Fluorescence Marking

By adding a DNA colorant, for example TOTO with a ratio of one TOT macromolecule to five DNA base pairs, the DNA is fluorescence-marked after approximately 10 minutes at room temperature. To this end, water/buffer containing the corresponding amount of TOTO is purged into the chamber. For observing the bands, and Axiovert 100 of the Carl Zeiss company was used. The two bands of the oligomers having a length of 40 bp and 80 bp respectively were observable.

EXAMPLE 2

Preparation of a Cationic Monolayer or Bilayer by Means of a Langmuir-Blodgett Technique By means of the Lanfmuir-Blodgett technique, a fluid membrane was applied to PMMA; instead of PMMA, also PC, PE, PS, PVA as well as cyclic olefins were used. In the Langmuir-Blodgett technique, amphiphilic molecules solved in chloroform are spread on the water surface of a trough made of teflon so that the hydrophilic portion of the molecule penetrates the water and the hydrophobic part projects from the water. This system can be compressed to the desired lateral pressure by means of an appropriate barrier. If now a vertically oriented platelet made of the above-mentioned materials is dipped into the water through this film, a fluid monolayer forms on the surface of the platelet.

The same experiments as in example 1 were carried our with this substrate supported membrane and the same results were obtained.

EXAMPLE 3

A substrate supported membrane according to Example 1 or Example 2 was prepared.

Separation of the DNA by Cross Fields

Contrary to the first and second examples, cross fields, i.e. a constant field superimposed by an alternating field instead of a pulsed field was applied for the separation of the DNA80 bp and the DNA 40 bp.

To this end, the constant field exhibited a field strength between 2 and 200 V/cm, the AC voltage field had a field strength between 2 and 200 V/cm at a frequency from 0.1 to 100 Hz. Thereby, platinum/platinum black or alternatively Ag/AgCl electrodes were used.

The same experiments as in example 1 were performed with the substrate supported membrane and the same results were obtained.

EXAMPLE 4

A substrate supported membrane according to Example 1 or Example 2 was prepared

Separation of the DNA by Structuring the Substrate

The membrane is applied to a previously structured substrate as is shown, for example, in FIG. 3 and is described with reference to this Figure. This substrate comprised ripple marks or a roughness having a height of approximately 0.1 nm and a periodicity of about 100 nm. Moreover, the used substrates were transparent and had a thickness from 100 μm to 200 μm. The electrode assembly was driven as in Example 3.

The results received with this arrangement correspond to the result obtained in Example 3, wherein the relative distance between the bands was larger.

EXAMPLE 5

Collecting the DNS on a Line by Providing Non-Fluid Areas

Parts of the chamber floor were coated with materials, on which the applied membrane is non-fluid, as is described in the Examples 1–4. To this end, for example $Al_2O_3P$ or PMMA were used. These areas represent an exclusion area for the DNA macromolecules that are mobile on the membrane. By applying an electrical field forcing the DNA in the direction of the exclusion area, the DNA macromolecules can be collected at the boundary between the membrane and the exclusion area.

By means of this membrane, and electrophoretic separation as in Example 1 was performed. In the result, sharper bands were observed, i.e. bands having an extension in the direction of the field that is less than the extension of the bands obtained in Example 1.

EXAMPLE 6

Collecting the DNS on a Line by Providing Areas that are not Wetted by the Membrane By applying $Al_2O_3$ on a predetermined portion of the chamber floor with a height of 10 nm to 1 μm and a width of 1–30 μm, the formation of a membrane in this portion was prevented. Hereby, the same experiments as in Example 1 were performed and the same results as in Example 5, i.e. sharper bands, were obtained.

The invention claimed is:

1. A method for the electrophoretic separation of particles, particularly of membrane-adherent macromolecules, the method comprising:
    applying the particles to a substrate-supported membrane such that the particles are mobile across a surface of the substrate-supported membrane;
    providing an electrical field having a direction that is oriented along the surface across which the particles are mobile; and
    performing electrophoresis according to at least one of:
        temporarily modifying at least one of the strength and the direction of the electrical field such that a resulting force acts on the particles causing movement among the particles that depends on the length of the particles, and
        using a substrate supporting the substrate-supported membrane that has a structured membrane-compatible surface that provides a force acting on the moving particles that depends on the length of the particles.

2. A method according to claim 1, wherein the substrate-supported membrane is a fluid lipid membrane, particularly comprising at least one of the lipids activated by PEG and DAC-Chol lipids.

3. A method according to claim 2, wherein the fluid lipid membrane is a cationic fluid lipid membrane.

4. A method according to claim 2, wherein the fluid lipid membrane includes amphiphilic macromolecules.

5. A method according to claim 2, wherein the fluid lipid membrane includes bilayers of charged lipids.

6. A method according to claim 1, wherein the electrical field is a pulsed electrical field.

7. A method according to claim 1, wherein the electrical field is an alternating field on which a time constant field is superimposed.

8. A method according to claim 7, wherein the alternating field and the time constant field are superimposed in a crosswise manner.

9. A method according to claim 1, wherein the structured membrane-compatible surface including ribs, supporting the membrane.

10. A method according to claim 9, wherein the substrate exhibits a periodicity ranging from 2 nm to 200 nm.

11. A method according to claim 9, wherein the ribs have a height in the range of 1 nm to 10 nm.

12. A method according to claim 9, wherein the electrical field is a time constant field having a direction that is substantially parallel to the ribs.

13. A method according to claim 1, wherein said movement is a rotation.

14. A method according to claim 1, wherein:
    the substrate includes an exclusion area in which the particles are not mobile; and
    the method further comprises collecting the particles at said exclusion area upon providing the electrical field, prior to performing the electrophoresis.

15. A method according to claim 14, wherein:
    the substrate-supported membrane is a fluid lipid membrane, particularly comprising at least one of the lipids activated by PEG and DAC-Chol lipids; and
    the exclusion area is a non-fluid area of the fluid lipid membrane.

16. A method of observing an electrophoretic separation, comprising:
    performing the method for the electrophoretic separation of particles of claim 1;
    recording digitized image data of the electrophoretic movement; and
    evaluating the recorded image data using a computer.

17. A method according to claim 1, wherein the particles to be separated include at least one of DNA, RNA, DNA-oligomers, RNA-oligomers, and proteins.

18. A method according to claim 1, further comprising providing a pH gradient, wherein the particles migrate according to the pH gradient.

19. A method according to claim 18, wherein the pH gradient is provided parallel to the electrical field.

20. A method according to claim 18, wherein the pH gradient is provided substantially perpendicular to the electrical field.

* * * * *

UNITED STATES PATENT AND TRADEMARK OFFICE
CERTIFICATE OF CORRECTION

| | |
|---|---|
| PATENT NO. | : 7,204,922 B1 |
| APPLICATION NO. | : 10/049245 |
| DATED | : April 17, 2007 |
| INVENTOR(S) | : Kahl et al. |

It is certified that error appears in the above-identified patent and that said Letters Patent is hereby corrected as shown below:

Title Page item 76,
Inventors:
Change "Amallenstrasse" to --Amalienstrasse--
Change "Pelssenbergstr" to --Peissenbergstrasse--
Change "Römerholweg" to --Römerhofweg--
Change "Karisfeld" to --Karlsfeld--
Change "Leberbiümchenstr" to --Leberblümchenstrasse--

Title Page item 22,
PCT Filed:
Change "Jul. 26, 1999" to -- Jul. 26, 2000--

Signed and Sealed this

Twenty-third Day of October, 2007

JON W. DUDAS
*Director of the United States Patent and Trademark Office*